United States Patent
Wu et al.

(10) Patent No.: US 10,094,978 B2
(45) Date of Patent: Oct. 9, 2018

(54) HIGH POWER TERAHERTZ PHOTOCONDUCTIVE ANTENNA ARRAY

(71) Applicant: The Government of the United States of America, as represented by the Secretary of the Navy, Arlington, VA (US)

(72) Inventors: Dong Ho Wu, Olney, MD (US); Benjamin Graber, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 223 days.

(21) Appl. No.: 15/191,299

(22) Filed: Jun. 23, 2016

(65) Prior Publication Data
US 2016/0377803 A1    Dec. 29, 2016

Related U.S. Application Data

(60) Provisional application No. 62/183,558, filed on Jun. 23, 2015.

(51) Int. Cl.
*G02B 6/10*    (2006.01)
(52) U.S. Cl.
CPC ...................................... *G02B 6/10* (2013.01)
(58) Field of Classification Search
CPC ........... G02B 6/10; G02B 6/4296; G02B 7/00
See application file for complete search history.

(56) References Cited

U.S. PATENT DOCUMENTS

| | | | |
|---|---|---|---|
| 5,729,017 | A | 3/1998 | Brener et al. |
| 9,177,685 | B1 | 11/2015 | Wu et al. |
| 2006/0152412 | A1 | 7/2006 | Evans et al. |
| 2007/0194253 | A1 | 8/2007 | Nishizawa et al. |
| 2008/0315098 | A1 | 12/2008 | Itsuji |
| 2009/0283680 | A1 | 11/2009 | Logan |
| 2014/0240510 | A1 | 8/2014 | Takenaka |
| 2014/0264032 | A1 | 9/2014 | Neshat |
| 2015/0171970 | A1 | 6/2015 | Nakayama |

OTHER PUBLICATIONS

International Search Report and Written Opinion for PCT/US2016/039047 from the International Searching Authority, dated Oct. 14, 2016.

(Continued)

*Primary Examiner* — David Porta
*Assistant Examiner* — Faye Boosalis
(74) *Attorney, Agent, or Firm* — US Naval Research Laboratory; William P. Ladd

(57) ABSTRACT

Systems and method are provided for producing portable, high power, broadband terahertz emitters based on arrayed terahertz photoconductive antennas. After such an arrayed structure is made, the phase of terahertz signals that are produced by each photoconductive antenna can be adjusted, and the terahertz signals can be added such that the signals are added constructively. Terahertz emitters based on terahertz photoconductive antenna arrays are advantageously small in size and scalable, allowing for terahertz power to be increased by adding more photoconductive antenna arrays.

20 Claims, 16 Drawing Sheets

(56) References Cited

OTHER PUBLICATIONS

International Preliminary Report on Patentability for PCT/US2016/039047 from the Internationl Bureau, dated Jan. 4, 2018.

"Coherent and incoherent terahertz beams measured from a terahertz photoconductive antenna," Dong Ho Wu, Benjamin Graber, Christopher Kim, S. B. Qadri, and Anthony Garzarella, Appl. Phys. Lett. 104, 051126 (Feb. 2014).

"Failure mechanism of THz GaAs photoconductive antenna," Syed B. Qadri, Dong H. Wu, Benjamin D. Graber, Nadeemullah A. Mahadik, and Anthony Garzarella, Appl. Phys. Lett. 101, 011910 (Jul. 2012).

"Dicke effect in a multi-ripple wave guide," H. Lee and L. E. Reichl, Phys. Rev. B 77 205318 (May 2008).

"Transient photoconductivity in GaAs as measured by time-resolved terahertz spectroscopy," Matthew C. Beard, Gordon M. Turner, and Charles A. Schmuttenmaer; Phys. Rev. B 62, 15764 (Dec. 2000).

"Ultrafast high-field carrier transport in GaAs measured by femtosecond pump-terahertz probe spectroscopy," Shi, Yulei, Zhou, Qing-li, Zhang, Cunlin, and Jin, Bin; Applied Physics Letters, 93, 121115 (Sep. 2008).

"Generation and detection of terahertz radiation up to 4.5 THz by low-temperature grown GaAs photoconductive antennas excited at 1560 nm," Rämer, Jan-Martin, Ospald, Frank, von Freymann, Georg, and Beigang, René; Applied Physics Letters, 103, 021119 (Jul. 2013).

"Cherenkov Radiation from Femtosecond Optical Pulses in Electro-Optic Media;" D. H. Auston, K. P. Cheung, J. A. Valdmanis, and D. A. Kleinman; Phys. Rev. Lett. 53, 1555; (Oct. 1984).

"Novel sources and detectors for coherent tunable narrow-band terahertz radiation in free space," Aniruddha S. Weling and David H. Auston, J. Opt. Soc. Am. B 13, 2783-2792 (Dec. 1996).

"Generation and detection of ultrabroadband terahertz radiation using photoconductive emitters and receivers," Shen, Y. C.. Upadhya, P. C., Beere, H. E., Linfield, E. H., Davies, A. G., Gregory, I. S., Baker, C., Tribe, W. R. and Evans, M. J., Applied Physics Letters, 85, 164-166 (Jul. 2004).

"Significant performance enhancement in photoconductive terahertz optoelectronics by incorporating plasmonic contact electrodes," C.W. Berry, N. Wang, M.R. Hashemi, M. Unlu, and M. Jarrahi; Nat. Commun. 4, 1622 (Mar. 2013).

"Observation of Gigawatt-Class THz Pulses from a Compact Laser-Driven Particle Accelerator," A. Gopal, S. Herzer, A. Schmidt, P. Singh, A. Reinhard, W. Ziegler, D. Brommel, A. Karmakar, P. Gibbon, U. Dillner, T. May, H-G. Meyer, and G. G. Paulus; Phys. Rev. Lett. 111, 074802 (Aug. 2013).

"Impulse response of photoconductors in transmission lines," Auston, D.H.; Quantum Electronics, IEEE Journal of, vol. 19, No. 4, pp. 639,648 (Apr. 1983).

"Picosecond photoconducting Hertzian dipoles," Auston, D. H., Cheung, K. P., and Smith, P. R., Applied Physics Letters, 45, 284-286 (May 1984).

"Temperature dependence of femtosecond electromagnetic radiation from semiconductor surfaces," Hu, B. B., Zhang, X.-C., and Auston, D. H., Applied Physics Letters, 57, 2629-2631 (Dec. 1990).

"Tunable, continuous-wave Terahertz photomixer sources and applications," Preu, S., Dohler, G. H., Malzer, S., Wang, L. J., and Gossard, A. C., Journal of Applied Physics, 109, 061301 (Mar. 2011).

"Enhancement of the output power of a terahertz parametric oscillator with recycled pump beam," Wu, Dong Ho and Ikari, Tomofumi, Applied Physics Letters, 95, 141105 (Oct. 2009).

"Failure mechanism of THz GaAs photoconductive antenna," Qadri, Syed B., Wu, Dong H., Graber, Benjamin D., Mahadik, Nadeemullah A., and Garzarella, Anthony, Applied Physics Letters, 101, 011910 (Jul. 2012).

"Highly tunable fiber-coupled photomixers with coherent terahertz output power," Verghese, S.; McIntosh, K.A.; Brown, E.R., Microwave Theory and Techniques, IEEE Transactions on , vol. 45, No. 8, pp. 1301,1309 (Aug. 1997).

"GaAs under Intense Ultrafast Excitation: Response of the Dielectric Function," Li Huang, J. Paul Callan, Eli N. Glezer, and Eric Mazur, Phys. Rev. Lett. 80, 185 (Jan. 1998).

S. Preu et al., Tunable, Continuous-wave Terahertz Photomixer Sources and Applications, J. Appl. Phys. 109, 06131 (2011).†

E.R. Brown, THz Generation by Photomixing in Ultrafast Photoconductors, 13 Int. J. of High Speed Electronics & Systems 497 (2003).†

† cited by third party

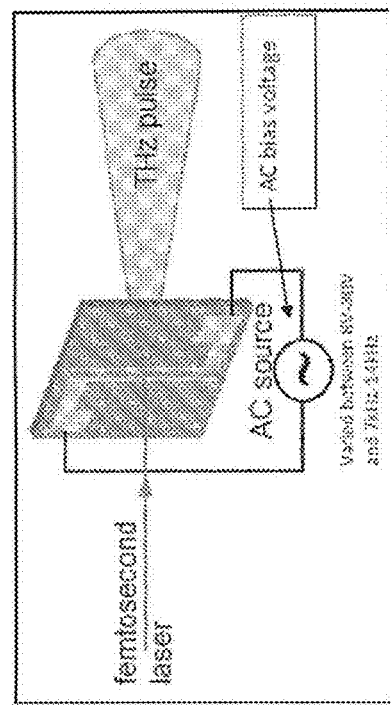
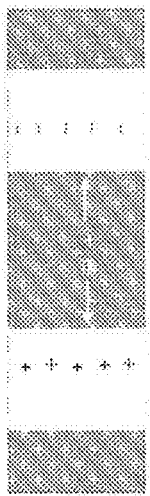
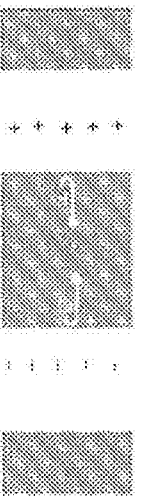
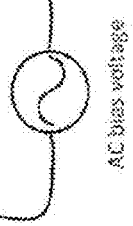
Figure 2A
Figure 2(B1)
Figure 2(B2)
Figure 2(B3)
Figure 2B

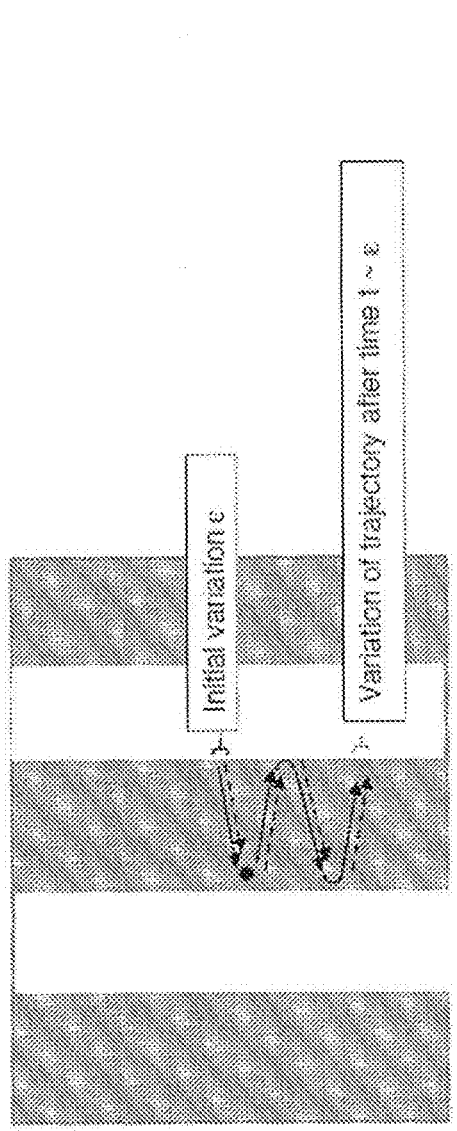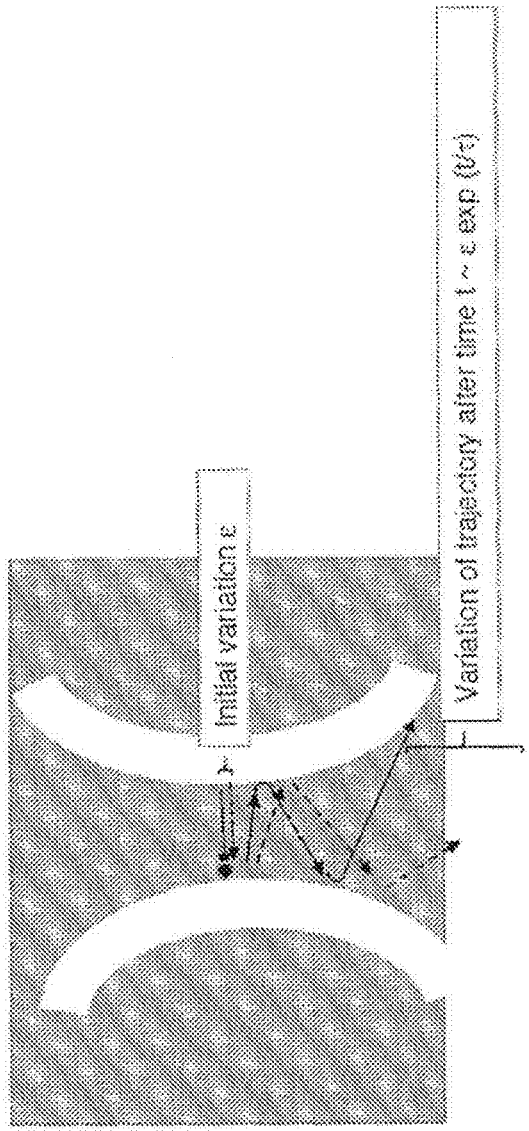
Figure 7a
Figure 7b

HIGH POWER TERAHERTZ PHOTOCONDUCTIVE ANTENNA ARRAY

CROSS REFERENCE TO RELATED APPLICATIONS

This application claims the benefit of U.S. Provisional Patent Application No. 62/183,558, filed on Jun. 23, 2015, which is incorporated by reference herein in its entirety.

FIELD OF THE DISCLOSURE

The present disclosure relates generally to terahertz photoconductive antennas, and more specifically relates to optimizing a terahertz photoconductive antenna design to produce a strongly coherent terahertz beam.

BACKGROUND

Terahertz photoconductive antennas have been used for more than two decades. Since its invention in 1984, minor modifications have been made to the antenna structures; however, details of the antenna design and the parallel micro-strip-line electrodes, which form the basic electrode structure of the conventional photoconductive antenna, have not been modified and are still being used.

FIG. 1 is a prior art terahertz photoconductive antenna structure 100. The parallel electrodes 105 are typically fabricated by depositing gold layers into two parallel trenches. Although the trench depth in FIG. 1 and the gold electrode thickness are labeled as 650 nm and 520 nm, the depth and thickness of the commercial photoconductive antennas have not been optimized, and there is no standard for these values. Therefore, it is not uncommon to see a large variation in these parameters from photoconductive-antenna manufacturers, and there are few guidelines for the fabrication of electrodes. The gold electrodes can often be excessively deposited, so that their thickness exceeds 1 µm. In commercial photoconductive antennas, the gold layers (electrodes) directly contact the trench walls, so that electric currents can flow from the electrode through the sidewall of the trench.

FIG. 2A is a prior art diagram representing the generation of a terahertz pulse using a femto-second laser and a photoconductive antenna. FIG. 2B is a prior art diagram representing the positive and negative charges between the electrodes during the generation of a terahertz pulse. FIG. 3 is a prior art diagram of a cross-sectional view of photoconductive antenna showing the photocurrents, bias currents and thermal currents during the generation of a terahertz pulse. FIGS. 2A and 3 illustrate that the terahertz pulse can be produced by illuminating a semiconductor slab (e.g., a GaAs substrate) with a femto-second laser beam. The laser pulse can generate a surface plasma, consisting of positive charges and negative charges. This oscillating surface plasma is known as a surface plasmon. The oscillating positive and negative charges can generate the terahertz pulse.

If the positive and negative charges recombine immediately after they are produced, the intensity of the terahertz pulse becomes very weak. Therefore, in order to minimize the charge recombination, a bias voltage can be applied to the electrodes, which can create an electric field that separates the positive charges from the negative charges (see FIG. 2(B1)). The positive charges will be attracted to the negative electrode, and the negative charges will be attracted to the positive electrode. However, when these charges arrive at the electrodes, they will ordinarily be discharged. To prevent such a discharge, the polarity of the electrodes can be switched right before the charges touch the electrodes, or just before they collide and recombine (see FIG. 2(B2) and FIG. 2(B3)). In other words, an AC bias voltage with an optimum frequency can substantially enhance the oscillation amplitude of the plasmon (the photocurrent) so that it increases the terahertz pulse strength.

The ac bias voltage, however, can result in substantial bias current flowing between the electrodes. This bias current, along with the photocurrent, can generate considerable Joule heating. The Joule heating, together with the thermal energy provided by the femto-second laser beam, can create thermal electric currents, which are incoherent in nature. The photocurrent, bias currents and thermal electric currents can all produce Joule heat, and the Joule heat can create more thermal currents, which can produce blackbody radiation, such as incoherent terahertz beams and infrared beams.

The thermal electric currents can also disrupt the coherency of the photocurrent and the bias currents, so that it reduces the strength of the coherent terahertz beam, and enhances the incoherent terahertz beam. This further increases the heating and the thermal electric currents. FIG. 4 is a prior art schematic diagram the explains how the photocurrent, bias-current, and thermal currents affect the production of a coherent terahertz beam and an incoherent terahertz beam. Specifically, FIG. 4 depicts the complex recursive process and the interactions among the three different currents. If the heat produced through this recursive process is excessive, it will eventually destroy the photoconductive antenna.

When a thermal electron (or electron wave function) travels perpendicular to the electrodes, in between a pair of parallel electrodes, the electron (or electron wave function) is likely to follow a bouncing ball trajectory or a standing wave pattern. FIG. 5A represents a bouncing ball trajectory for an electron wave function. FIG. 5B represents a standing wave pattern for an electron wave function. Therefore, the particle (the electron) or wave (the electron wave) is likely to be trapped in between the electrodes, unless the particle or wave travels at an oblique angle, such as in FIG. 6A and FIG. 7A. FIG. 6A represents a traveling ball mode trajectory for an electron wave function, and, similarly, FIG. 7A represents a non-chaotic trajectory, such as the traveling ball mode, for an electron wave function. Therefore, with the parallel electrode geometry, a large number of thermal electrons that flow incoherently can be trapped in between the electrodes and disrupt the photocurrent. FIG. 8A represents a slowly traveling, or virtually trapped, wave pattern for a traveling ball mode trajectory for an electron wave function.

Additionally, FIG. 6B represents a trapped ball mode trajectory for an electron wave function, and the associated FIG. 8B represents a standing wave mode for a trapped ball mode trajectory for an electron wave function. Similarly to FIG. 6A and associated FIG. 8A, FIG. 6B and FIG. 8B show how a large number of thermal electrons that flow incoherently can be trapped in between the electrodes and disrupt the photocurrent, and may not allow traveling wave pattern.

Consequently, a conventional photoconductive antenna with a pair of parallel electrodes is highly inefficient in converting the femto-second laser pulse into a terahertz beam; and, therefore, is not efficient in producing a strong, coherent terahertz beam. Instead, because of the above-mentioned problems, the antenna structure with the conventional electrodes predominantly produces incoherent terahertz beams, and the efficiency of the conventional photoconductive antenna is therefore very poor.

In summary, the conventional terahertz photoconductive antennas have the following limitations and disadvantages: (1) the design parameters, such as the trench depth, the thickness of the electrode, and the thickness of the substrate, are not optimized; (2) the conventional photoconductive antenna with a pair of parallel electrodes produces a very weak, coherent terahertz beam (<<1 mW); (3) with a strong pump-laser beam and a large bias voltage applied to the electrodes, they produce excessively incoherent terahertz beams, which lead to the destruction of the photoconductive antenna; and (4) as a result, the lifetime of the conventional photoconductive antenna is short.

A free electron laser can produce a high power terahertz beam of which average power can exceed several hundred Watts. However, a free electron laser is very large and not portable at all. Further, the free electron laser all other terahertz sources can produce a terahertz beam of which average power at best a few mW.

BRIEF DESCRIPTION OF THE DRAWINGS/FIGURES

The accompanying drawings, which are incorporated in and constitute part of the specification, illustrate embodiments of the disclosure and, together with the general description given above and the detailed descriptions of embodiments given below, serve to explain the principles of the present disclosure. In the drawings:

FIG. 2A is a prior art diagram representing the generation of a terahertz pulse using a femto-second laser and a photoconductive antenna;

FIG. 2B is a prior art diagram representing the positive and negative charges between the electrodes during the generation of a terahertz pulse;

FIG. 7A represents a non-chaotic trajectory for an electron wave function;

FIG. 7B represents a chaotic trajectory for an electron wave function, in accordance with an exemplary embodiment of the invention;

Figure 1:
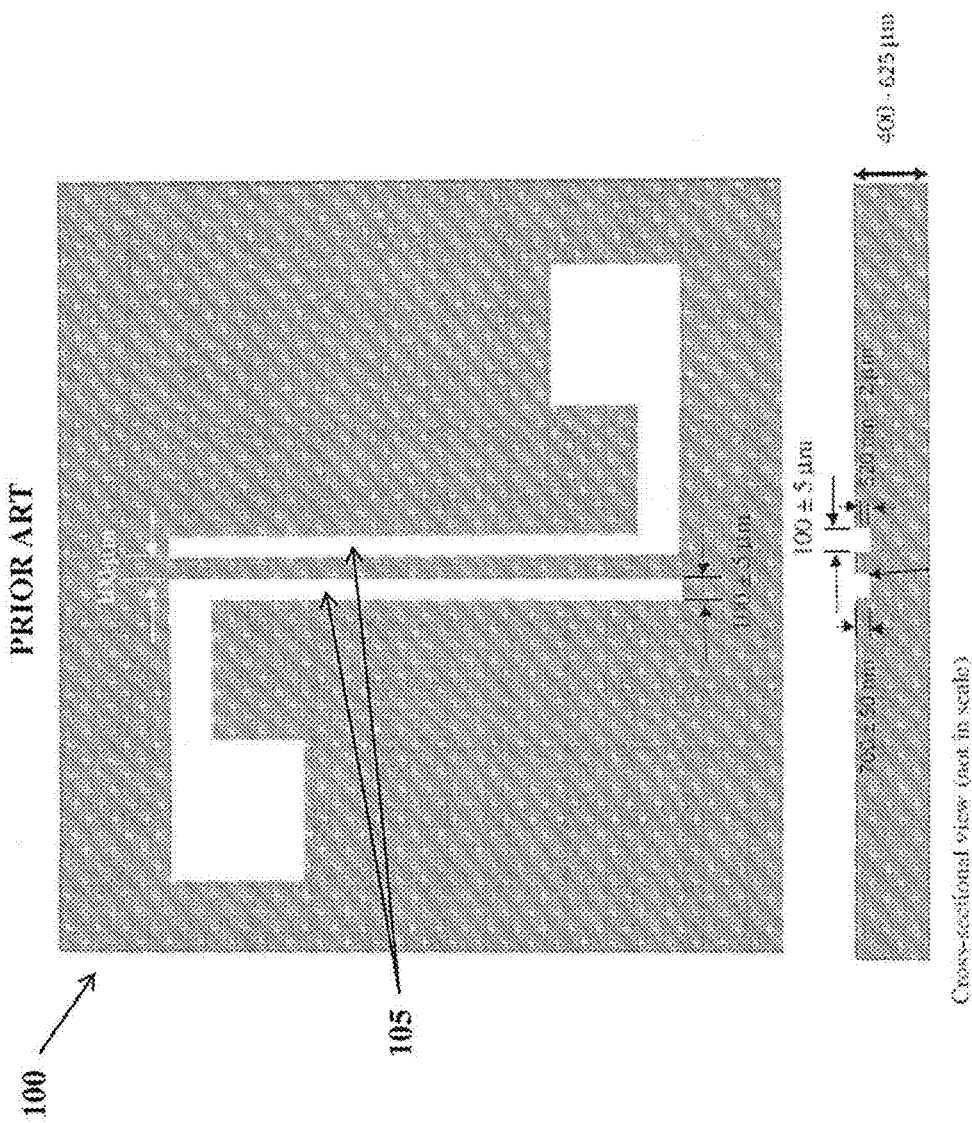
FIG. 1 is a prior art terahertz photoconductive antenna structure.
Figure 3:
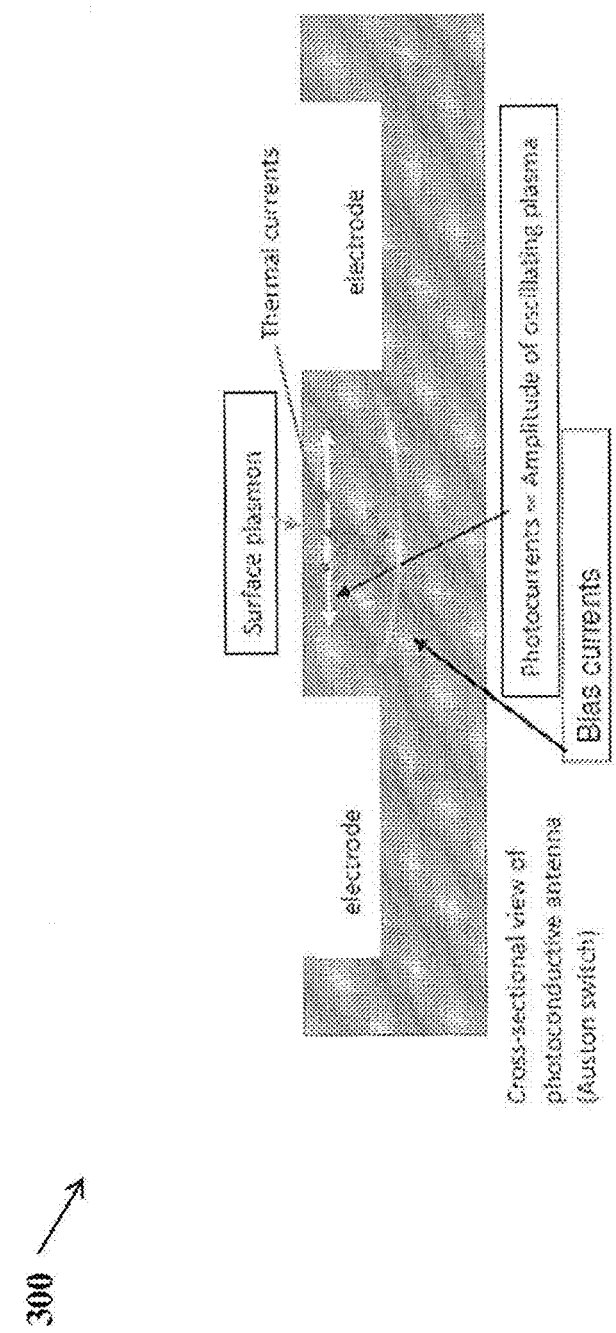
FIG. 3 is a prior art diagram of a cross-sectional view of photoconductive antenna showing the photocurrents, bias currents and thermal currents during the generation of a terahertz pulse.

Features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

In the following description, numerous specific details are set forth to provide a thorough understanding of the disclosure. However, it will be apparent to those skilled in the art that the disclosure, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring aspects of the disclosure.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of this discussion, the term "module" shall be understood to include one of software, or firmware, or hardware (such as circuits, microchips, processors, or devices, or any combination thereof), or any combination thereof. In addition, it will be understood that each module can include one, or more than one, component within an actual device, and each component that forms a part of the described module can function either cooperatively or independently of any other component forming a part of the module. Conversely, multiple modules described herein can represent a single component within an actual device. Further, components within a module can be in a single device or distributed among multiple devices in a wired or wireless manner. ps 1. Photoconductive Antennas With Chaotic Shape Electrodes One or more embodiments or implementations are hereinafter described in conjunction with the drawings, where like reference numerals refer to like elements throughout, and where the various features are not necessarily drawn to scale. As mentioned in the background section, the inefficiency of the conventional photoconductive antenna stems from the thermal electric currents, which are produced by both the thermal load of the femto-second laser beam and the electric currents, including the photocurrent, the bias current and the thermal electric current itself. It is also understood that the behavior of the thermal electric currents (and the heat production associated with these currents) is closely related with the electrodes. For example, by altering the design of the electrodes, one can suppress the production of thermal electrons, and minimize the disruption of the photocurrents by the thermal currents.

Accordingly, to improve the terahertz photoconductive antenna, the electrode design can be changed. First, a pair of trenches can be etched into a substrate. Then, in an exemplary embodiment of the invention, the electrode design of the terahertz photoconductive antenna can include two electrodes that are not parallel, instead of two parallel microstrip-line electrodes. Each one of the pair of non-parallel electrodes can be separately deposited into each of the pair of trenches in the substrate. That is, one electrode can go in one trench, and the other electrode can go in the other trench. Finally, the pair of non-parallel electrodes can be configured in the trenches to maintain an insulation layer, which can include either depositing a physical electrical insulation layer between each of the pair of non-parallel electrodes and the trench walls, or maintaining an air gap between each of the pair of non-parallel electrodes and the trench walls.

Figure 6B:
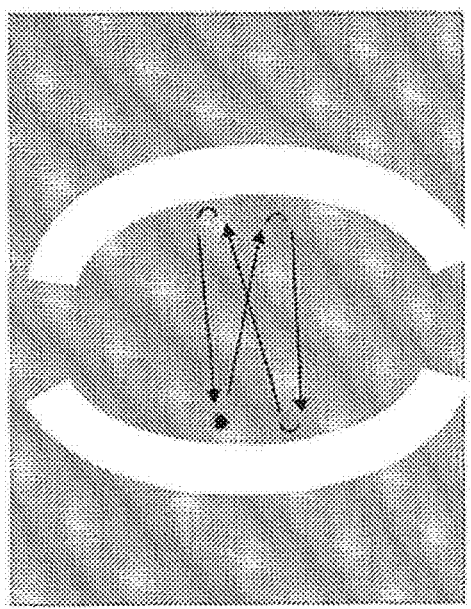
FIG. 6B represents a trapped ball mode trajectory for an electron wave function.
Figure 6C:
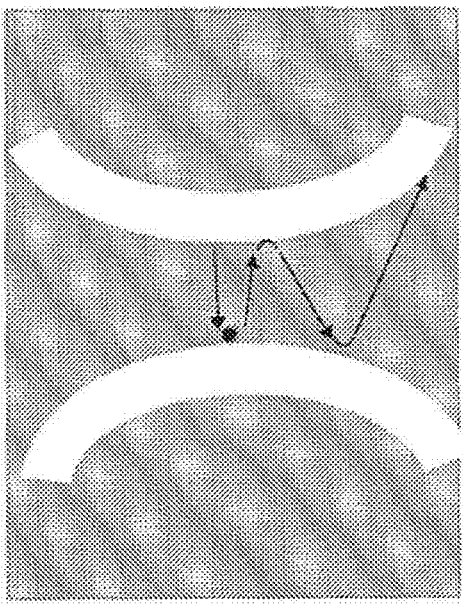
FIG. 6C represents a rapidly diverging ball mode trajectory for an electron wave function.
Figure 6A:
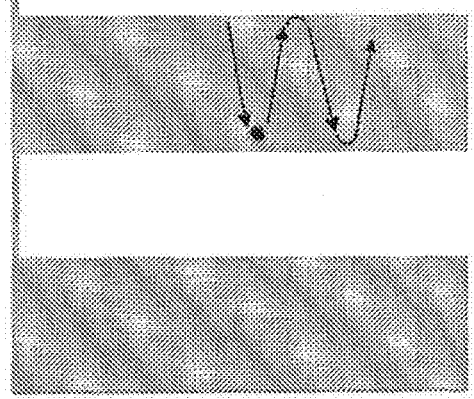
FIG. 6A represents a traveling ball mode trajectory for an electron wave function.
Figure 8B:
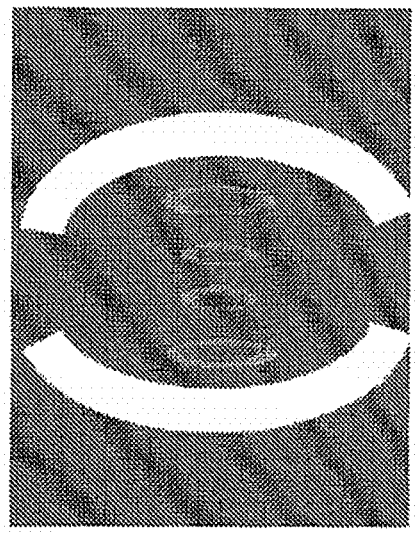
FIG. 8B represents a standing wave mode for a trapped ball mode trajectory for an electron wave function.
Figure 8C:
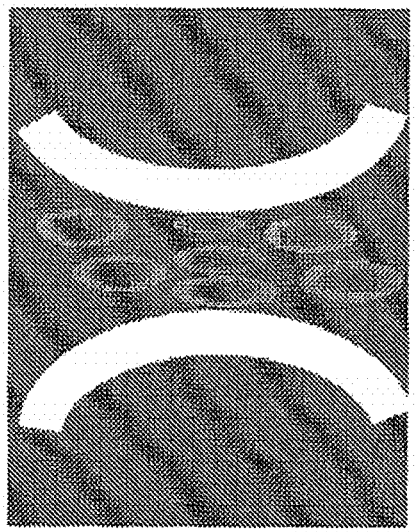
FIG. 8C represents a rapidly diverging wave pattern for a rapidly diverging ball mode trajectory for an electron wave function.
Figure 8A:
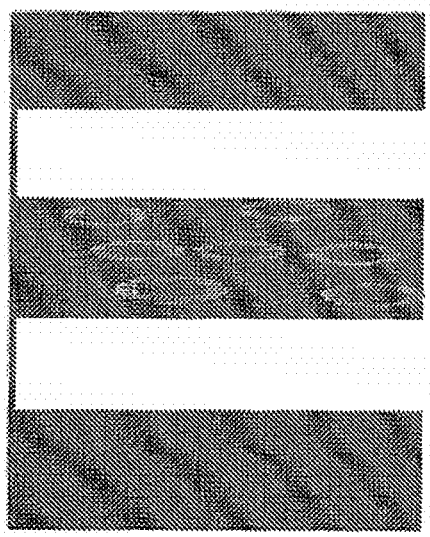
FIG. 8A represents a slowly traveling, or virtually trapped, wave pattern for a traveling ball mode trajectory for an electron wave function.

Several different, non-parallel shapes can be used in the design for the electrodes, and these shapes can be called "chaotic geometries" since, in contrast to a pair of parallel electrodes, these electrodes are configured to produce chaotic trajectories when a particle or wave bounces between the electrodes. The chaotic trajectory means that with a minute variation of the initial condition, the trajectory deviates, or varies, exponentially with time. FIG. 7B represents a chaotic trajectory for an electron wave function. In particular, FIG. 6C represents a rapidly diverging ball mode trajectory for an electron wave function, which represents an example of a chaotic trajectory. In association, FIG. 8C represents a rapidly diverging wave pattern for a rapidly diverging ball mode trajectory for an electron wave function.

Figure 4:
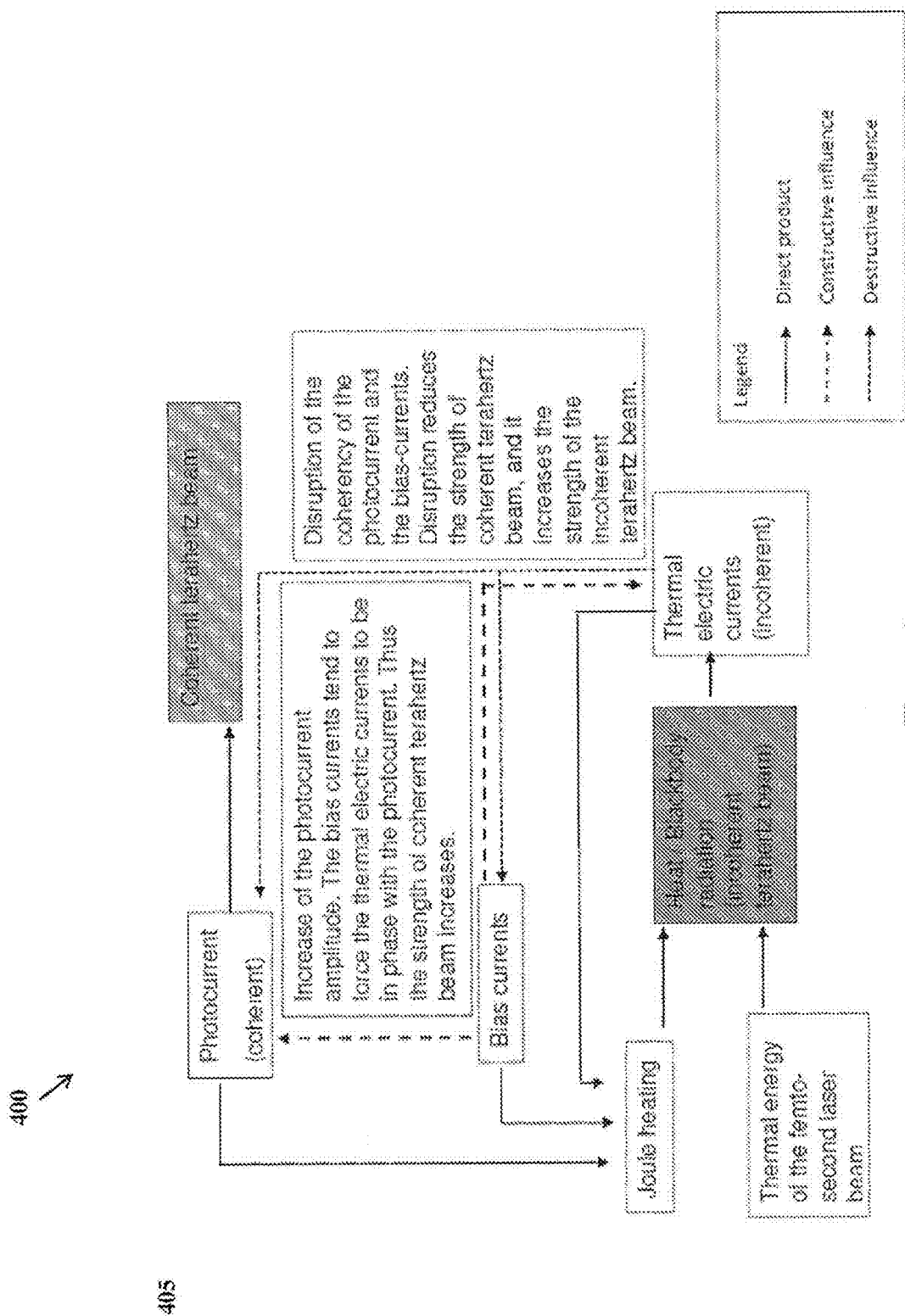
FIG. 4 is a prior art schematic diagram that explains how the photocurrent, bias-current, and thermal currents affect the production of a coherent terahertz beam and an incoherent terahertz beam.
Figure 5A:
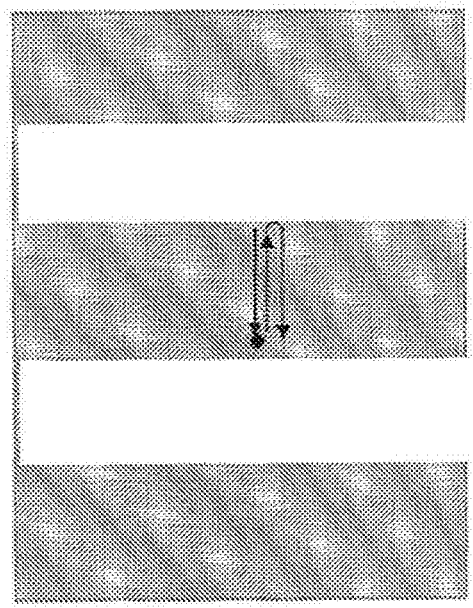
FIG. 5A represents a bouncing ball trajectory for an electron wave function.
Figure 5B:
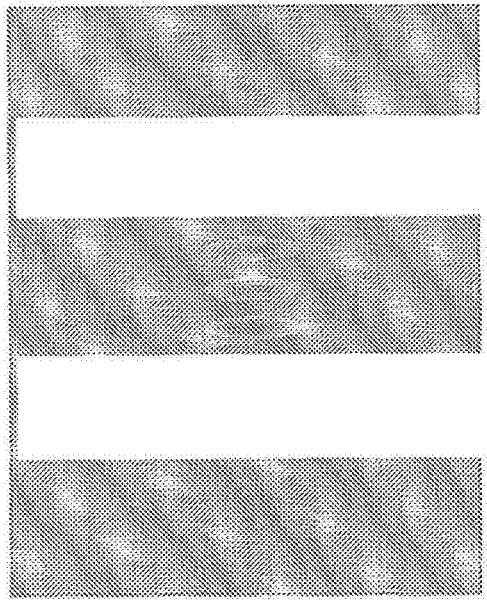
FIG. 5B represents a standing wave pattern for an electron wave function.

As explained in the background section with respect to the prior art schematic diagram in FIG. 4, there are three electric currents in a photoconductive antenna: the photocurrent, the bias currents and the thermal electric currents. These three currents interact with each other, either constructively or destructively. For example, the bias currents (or the electric field produced by the bias voltage) force the thermal electric currents to be in phase with the photocurrent, so that they can produce more of a coherent terahertz beam. However, the thermal electric currents tend to disrupt the coherency of the photocurrent and the bias currents, so that the strength of coherent terahertz beam is reduced and the strength of incoherent terahertz beam is increased.

In an exemplary embodiment of the invention, in a photoconductive antenna with a pair of chaotic electrodes, incoherent electric currents (e.g., thermal electric currents) normally follow chaotic trajectories, and their interference with the coherent electric currents become minimized. Therefore, it will promote some bias currents and some thermal electric currents to flow in phase with the coherent photocurrent, which can allow the photoconductive antenna to produce a stronger coherent terahertz beam.

Figure 9:
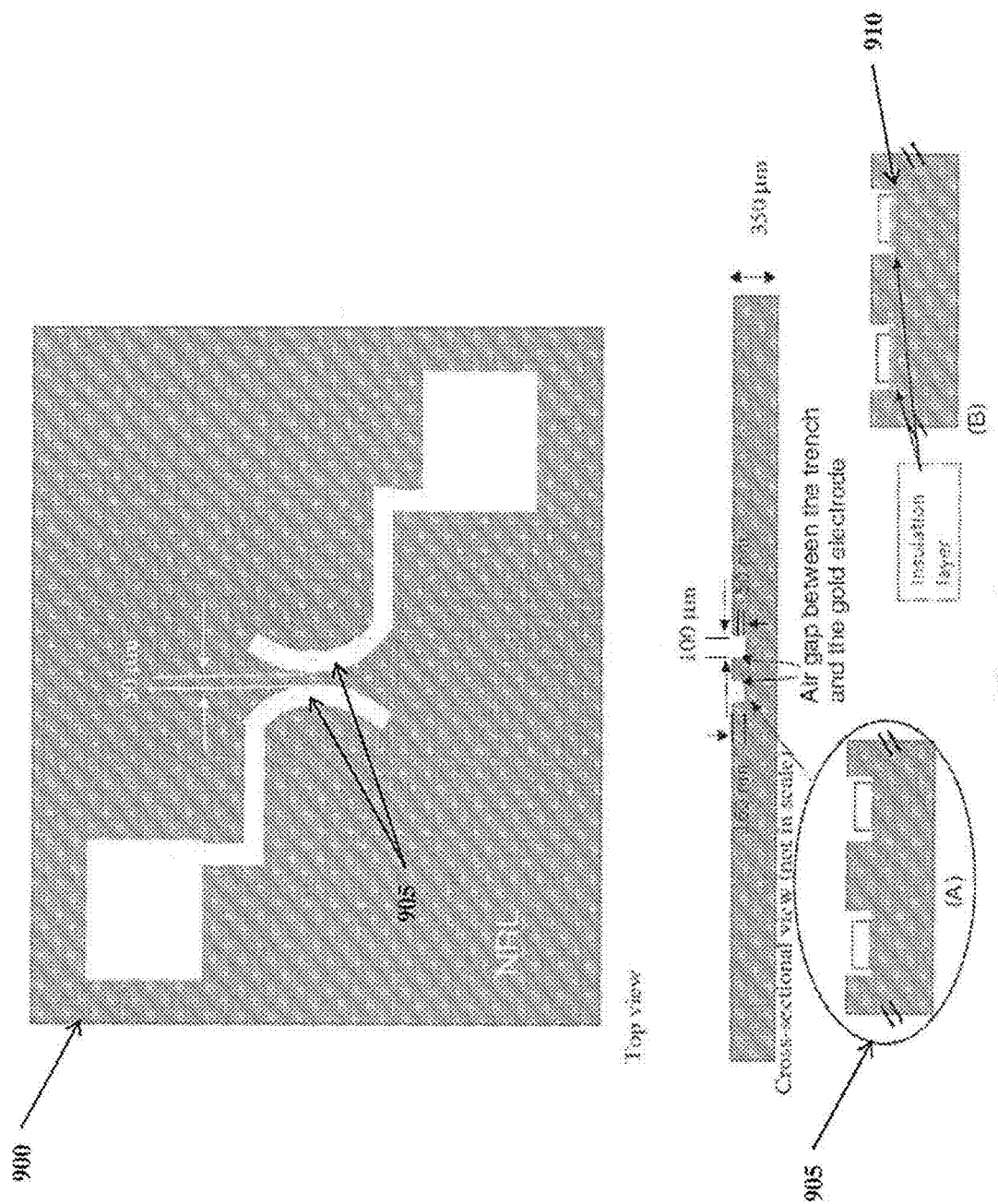
FIG. 9 is a photoconductive antenna with a pair of chaotic electrodes, in accordance with an exemplary embodiment of the invention.
Figure 10:
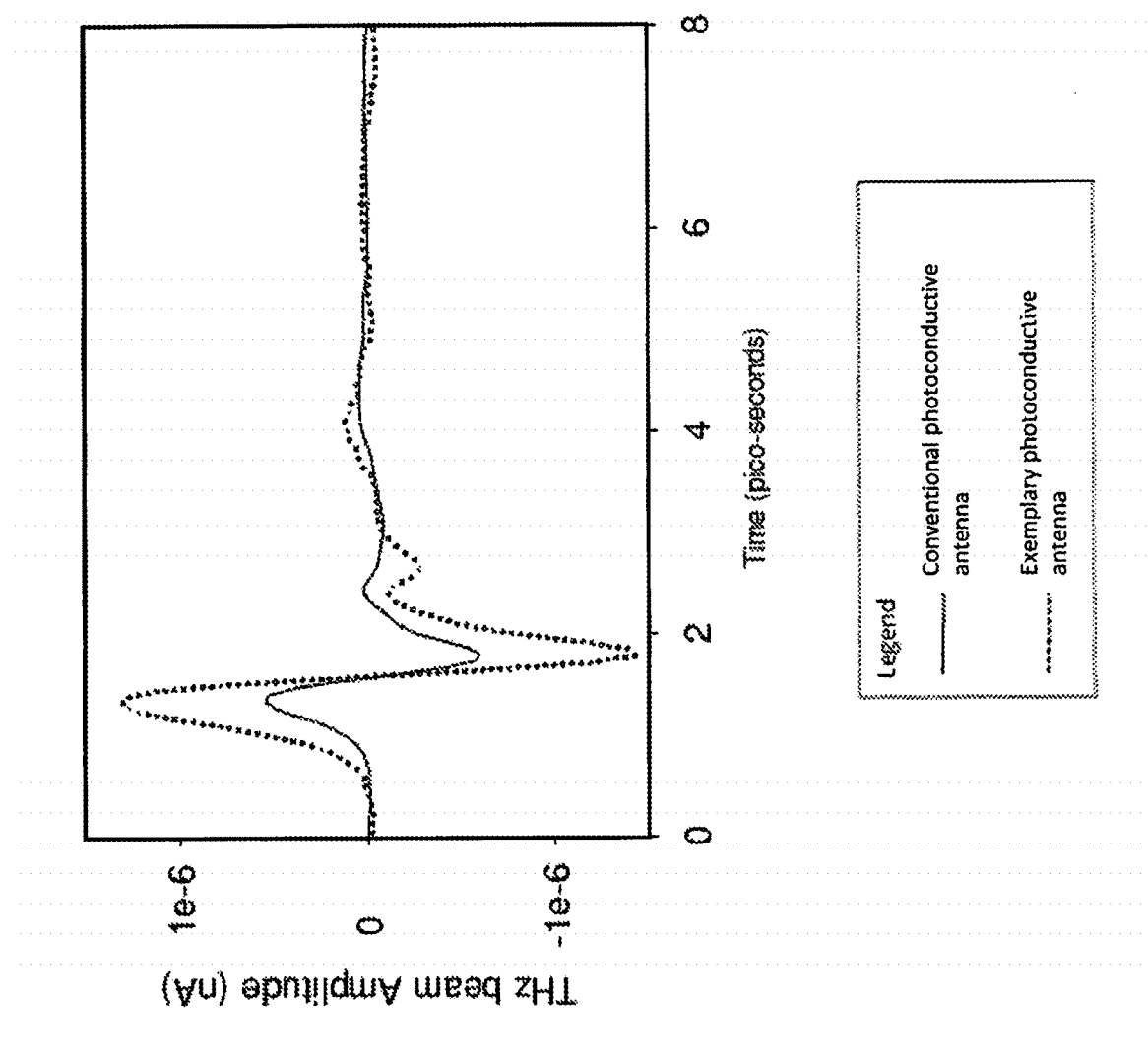
FIG. 10 is a graph comparing time domain signals from a conventional THz emitter and THz emitter in accordance with an exemplary embodiment of the invention.

In an exemplary embodiment of the invention, several different chaotic electrode geometries can be utilized. FIG. 9 is a photoconductive antenna 900 with a pair of chaotic electrodes 905, in accordance with an exemplary embodiment of the invention. Specifically, the chaotic electrodes in FIG. 9 represent an hourglass shape geometry that leads to chaotic trajectories (as also seen in FIG. 7B). FIG. 10 is a graph comparing time domain signals from a conventional THz emitter and THz emitter in accordance with an exemplary embodiment of the invention. Specifically, FIG. 10 is a graph of time domain signals from a conventional THz emitter with a conventional photoconductive antenna with a pair of parallel electrode (solid line) and an exemplary THz emitter with an exemplary photoconductive antenna with a pair of chaotic electrode (dotted line). Note that the exemplary THz emitter can produce a much greater coherent THz output (i.e., at least 3 mW THz output). Furthermore, the terahertz spectrum of the exemplary photoconductive antenna is nearly identical to that of the conventional photoconductive antenna, even while producing the much greater and more coherent THz output.

Figure 11:
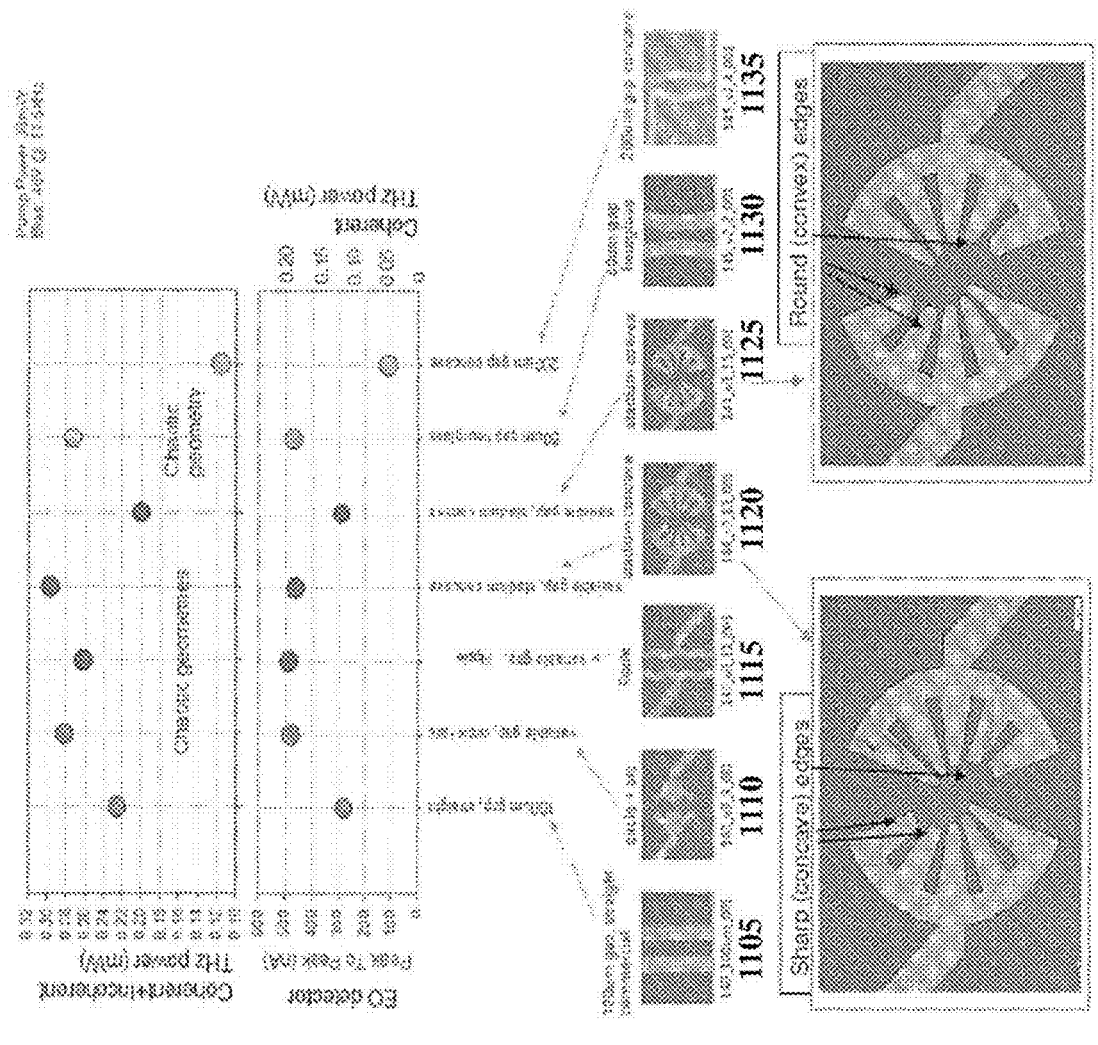
FIG. 11 is a chart of sample results obtained from photoconductive antennas with various geometries in accordance with an exemplary embodiment of the invention.

FIG. 11 is a chart of sample results obtained from photoconductive antennas with various geometries in accordance with an exemplary embodiment of the invention. Four antennas containing chaotic electrodes (i.e., circle plus arc electrode geometry 1110; a ripple electrode geometry 1115; a stadium concave geometry 1120; or a hourglass geometry 1130) produce much stronger terahertz beams when compared with three antennas with non-chaotic electrodes (i.e., a conventional parallel geometry 1105, a stadium convex geometry 1125, and a gap concave geometry 1135). Interestingly, drastically different results can be obtained from two antennas, stadium concave 1120 and stadium convex 1125, that look very similar to each other, except one, stadium concave 1120, has sharp edges and the other, stadium convex 1125, has round and smooth edges. The antenna with the stadium concave 1120 chaotic geometry leads to chaotic electron trajectories because its sharp edges reflect the electrons and do not allow them to enter into the slits.

Figure 12A:
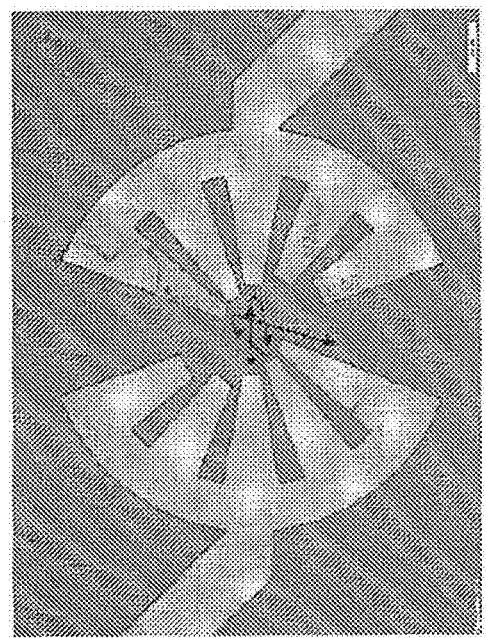
FIG. 12A is an example view of thermal electron behavior in a stadium concave geometry, in accordance with an exemplary embodiment of the invention.

FIG. 12A is an example view of thermal electron behavior in a stadium concave geometry, in accordance with an exemplary embodiment of the invention. The sharp edges of the stadium concave 1120 geometry force the electrons to follow spiral trajectories, as represented in FIG. 12A. Most thermal electrons reflected by the concave geometry follow chaotic trajectories, and diverge away from the emitter so that they minimally interfere with the photocurrent. Therefore, this emitter produces a relatively stronger terahertz beam.

Figure 12B:
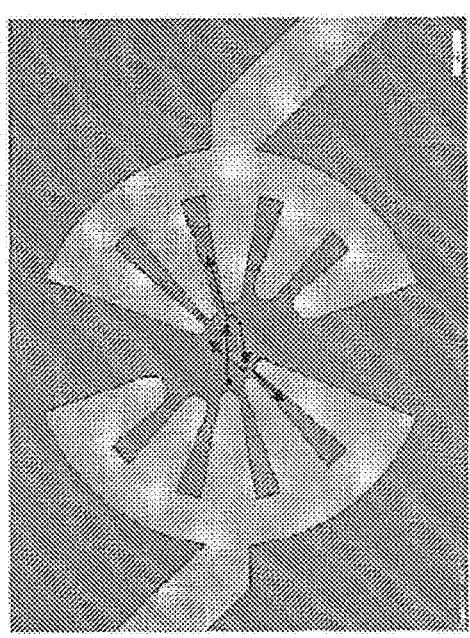
FIG. 12B is an example view of thermal electron behavior in a stadium convex geometry, in accordance with an exemplary embodiment of the invention.

By contrast, the smooth edges of the antenna with the stadium convex 1125 geometry make the electrons enter the slits, so that the electrons can eventually be trapped in the slits. FIG. 12B is an example view of thermal electron behavior in a stadium convex geometry, in accordance with an exemplary embodiment of the invention. These trapped electrons release their energy as heat, which disrupts the coherent electron currents and hence reduces the coherent terahertz beam output. Although the shape of the electrodes in FIG. 12B look similar to that of FIG. 12A, because of the convex tip of the electrodes, the thermal electrons tend to be trapped in the gaps between the electrodes. Consequently, they create more heat and disturb the photocurrent. Therefore, this emitter is inefficient and produces a weak terahertz beam. FIGS. 12A and 12B are included here to illustrate how the thermal electron behavior affects the performance of a terahertz emitter.

Figure 13:
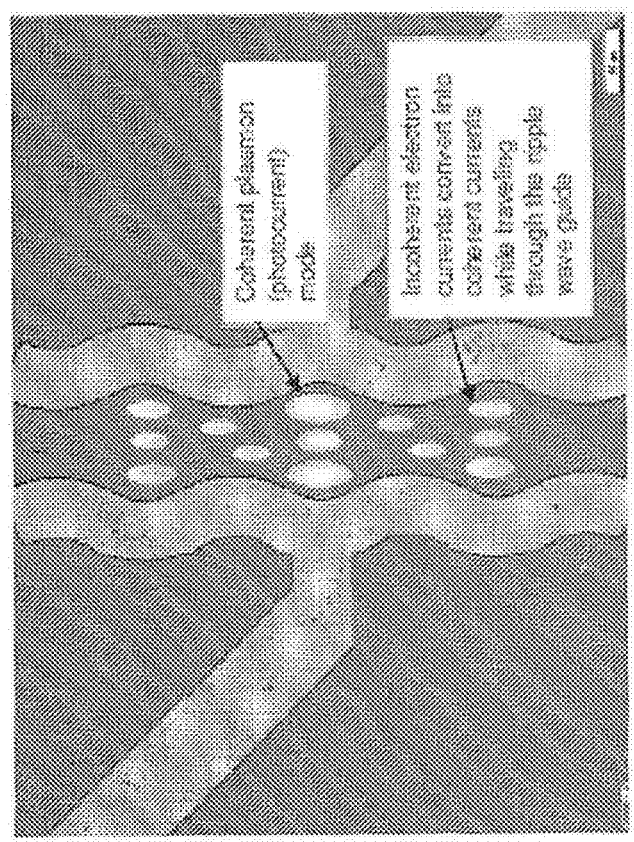
FIG. 13 is a graphic of how a ripple electrode geometry produces a more coherent terahertz beam, in accordance with an exemplary embodiment of the invention.

In an exemplary embodiment of the invention, a photoconductive antenna with a ripple chaotic electrode geometry can be the most efficient. The ripple chaotic electrode geometry includes a pair of wavy electrodes at a variable distance apart. The ratio of the coherent terahertz power to the total (coherent and incoherent) terahertz power for the ripple geometry is about 73% for the antenna. This is because a pair of ripple electrodes leads to chaotic electron trajectories. Furthermore, ripple electrodes not only minimize the interference between the incoherent electron currents and coherent currents, but also convert the incoherent electron currents into coherent currents, further amplifying the coherent electron currents, which produce a more coherent terahertz beam. FIG. 13 is a graphic of how a ripple electrode geometry produces a more coherent terahertz beam, in accordance with an exemplary embodiment of the invention.

In addition to altering the shapes of the electrodes as described above, the electrodes of the photoconductive antennas can be electrically insulated from the trench walls by air-gaps or by an electrical insulation layer, in accordance with an exemplary embodiment of the invention. FIG. 9 shows electrodes of the photoconductive antennas can be electrically insulated from the trench walls by air-gaps 905 or by an electrical insulation layer 910. With this electrical insulation, the electrodes can generate an electric field with a minimal bias current flowing between the electrodes. This exemplary photoconductive antenna can significantly reduce Joule heating; and, therefore, the thermal electrical currents, which can disrupt the coherent photocurrent. As a result, the exemplary photoconductive antenna can generate more of a coherent terahertz beam, and the incoherent terahertz-beam generation is considerably suppressed. In an exemplary embodiment of the invention, silicon-nitride (SiN) has been used as the material for an electrical insulation layer; however, one of ordinary skill in the art recognizes that other materials can be used as well.

For high-efficiency terahertz emission, the surface plasmon (the photocurrent) that produces the terahertz pulse should be generated at an optimum depth from the surface of the photoconductive antenna. Therefore, the depth of the electrodes that control the surface plasmon should be accordingly configured and optimized. In other words, the trench depth and the electrode thickness should be configured and optimized so that the surface plasmon is confined at the optimum depth from the surface. The depth of confinement is dependent on the electron mobility and the surface energy. If the trench depth is too deep or too shallow, and the thickness of the electrode is too thick or too shallow, they cannot control the surface plasmon effectively.

In addition, in an exemplary embodiment of the invention, a photoconductive antenna can use an optimum thickness of the GaAs substrate, so that the terahertz pulse can transmit through the GaAs substrate without suffering much transmission loss. If the GaAs substrate thickness is too thin, the femto-second laser beam will be able to penetrate through the substrate and deposit too much thermal energy onto the substrate, which eventually will lead to thermal damage to the substrate and destroy the photoconductive antenna. If the GaAs substrate is too thick, the terahertz beam will experience significant dissipation while passing through the substrate. To meet these design considerations the thickness of GaAs substrate, the trench depth of the electrodes, and the thickness of the gold electrodes for the exemplary photoconductive antenna is optimized.

Figure 14:
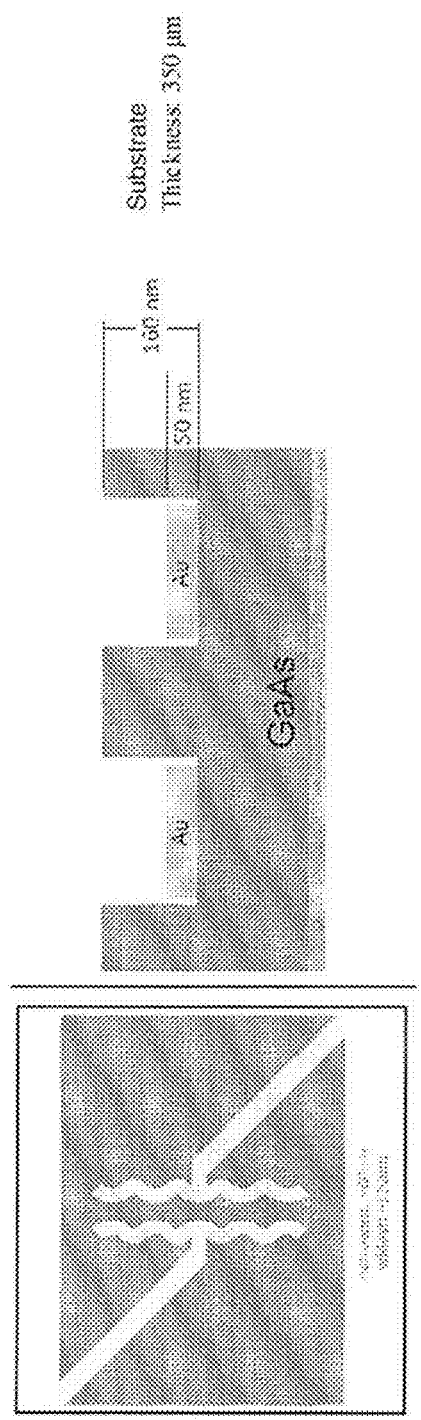
FIG. 14 is an example of an optimally configured photoconductive antenna, in accordance with an exemplary embodiment of the invention.

As noted, configuring an exemplary photoconductive antenna for an optimum depth of trench, optimum thickness of electrode, optimum thickness of the substrate is an important feature of the invention. FIG. 14 is an example of an optimally configured photoconductive antenna, in accordance with an exemplary embodiment of the invention. Specifically, the exemplary photoconductive antenna can be designed with a ripple electrode geometry with a substrate thickness of about 350 µm; a trench depth of about 160 nm; and an electrode thickness of about 50 nm. One of ordinary skill in the art will understand that these different parameters are just examples of an optimized exemplary photoconductive antenna, and values greater than or less than the values disclosed above can be utilized. Furthermore, the exemplary photoconductive antenna can include an air-gap between the electrode and the trench walls. The exemplary combination of features and parameters can produce a terahertz beam of at least 3 mW (average power), which is about 20-30 times stronger than the maximum average power a conventional terahertz emitter can currently produce.

In an exemplary embodiment of the invention, the exemplary terahertz photoconductive antennas described herein can be used for terahertz spectroscopy and imaging, which can enable new applications that were nearly impossible previously. Examples of these applications include detection and identification of biological and chemical agents, detection of hidden explosives, and detection and identification of environmental contaminants at a standoff distance. Another application currently being researched is to use the terahertz spectrometer to detect ionized air produced by a hidden nuclear material.

In addition to the applications discussed above, prototype devices for pharmaceutical applications in a real environment have been developed to see if terahertz spectrometers and terahertz imaging devices are able to screen for counterfeit drugs. The prototype device that consists of a conveyer belt, robotic arms, and a high-speed terahertz spectrometer can measure the terahertz spectrum of an unknown drug in order to determine whether its spectrum matches that of a legitimate drug. If the spectrum does not match, the robotic arm can reject the drug.

As noted herein, the maximum terahertz beam power produced by prior art photoconductive antennas is limited. A weak terahertz beam affects the spectroscopic resolution, the detection range, and the detection speed. Accordingly, it is imperative to increase the coherent terahertz-beam output for the above-mentioned applications.

One of ordinary skill in the art will understand that certain changes may be made to embodiments of the invention without departing from the scope and spirit of the invention. For example, while a GaAs substrate for the demonstration of the exemplary photoconductive antenna is described herein, other substrate materials for the photoconductive antenna can also be used. The electrode gap size can be in the range from a few tens of micrometers to a few hundred micrometers. The electrodes can be made of other metals than gold. The photoconductive antenna is described as a transmission mode terahertz emitter herein; however, one can slightly alter the design to demonstrate a reflection mode terahertz emitter.

In summary, the exemplary photoconductive antenna described herein does not produce much bias current or Joule heat; therefore, it can produce a strongly coherent terahertz beam. The exemplary photoconductive antenna can produce at least 3 mW of coherent terahertz radiation, whereas prior art photoconductive antennas could generate at best only 0.16 mW of coherent terahertz radiation. Furthermore, the exemplary photoconductive antenna can produce a wider bandwidth (i.e., 100 GHz to 3 THz) and a predominantly coherent terahertz beam. In addition, the lifetime of the exemplary photoconductive antenna is much longer than that of prior art versions. Overall, the features of the exemplary photoconductive antenna include (1) a pair of electrodes that lead to chaotic trajectories of incoherent electric currents, (2) an insulating layer, or air-gap, between the electrode and the trench walls, (3) optimum depth of trench, (4) optimum thickness of electrode, (5) optimum thickness of the substrate.

2. High Power Terahertz Photoconductive Antenna Array

As described above, terahertz photoconductive antennas can produce relatively high power, coherent terahertz beams. Embodiments of the present disclosure provide portable, high power, broadband terahertz emitters based on arrayed terahertz photoconductive antennas. After such an arrayed structure is made, the phase of terahertz signals that are produced by each photoconductive antenna can be adjusted, and the terahertz signals can be added such that the signals are added constructively.

Figure 15:
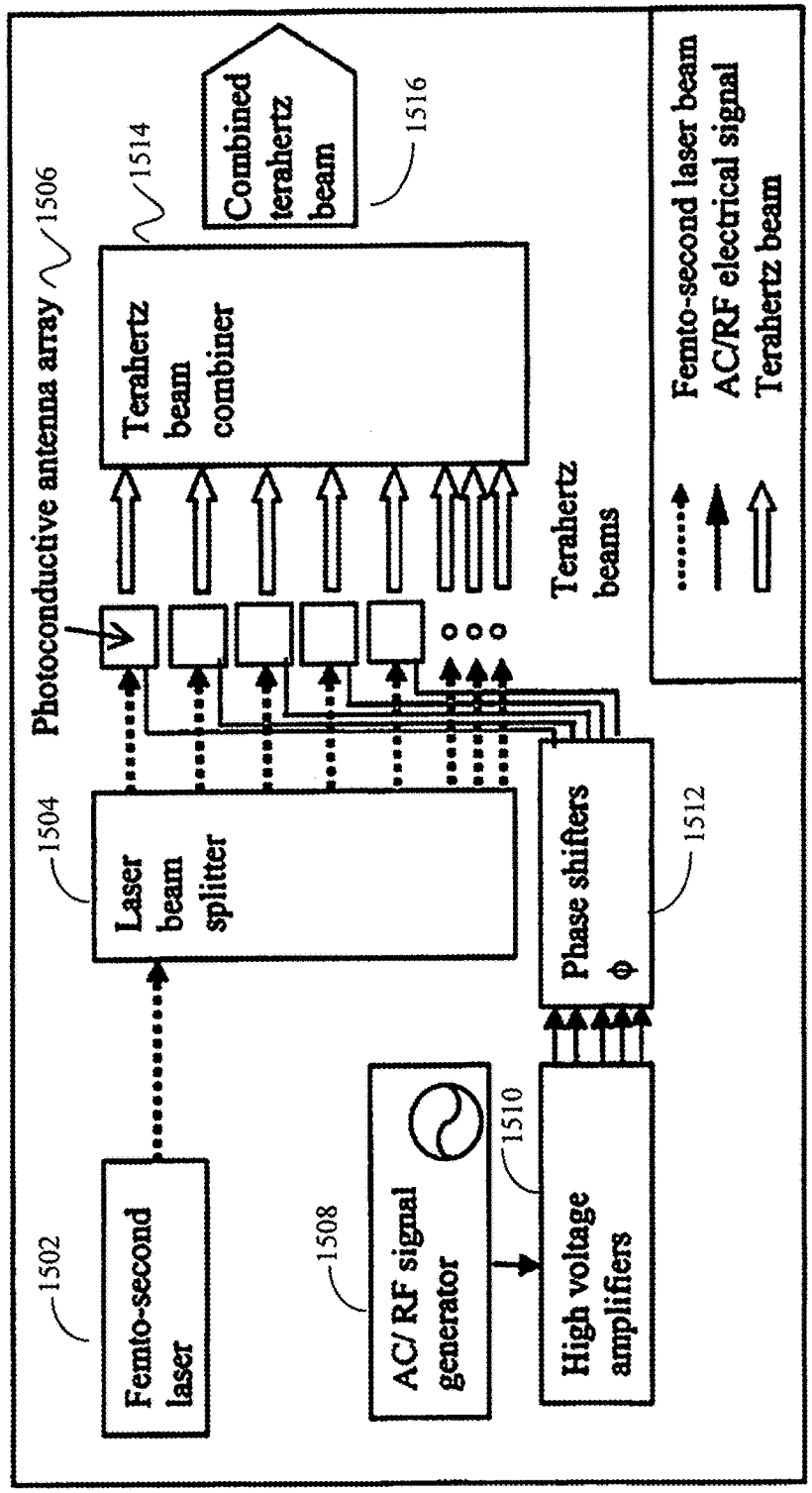
FIG. 15 is a schematic diagram of a high power terahertz emitter based on a photoconductive antenna array in accordance with an embodiment of the present disclosure.

FIG. 15 is a schematic diagram of a high power terahertz emitter based on a photoconductive antenna array in accordance with an embodiment of the present disclosure. In an embodiment, the high power terahertz emitter of FIG. 15 includes a laser 1502 (e.g., in an embodiment, a femtosecond laser as shown in FIG. 15), a laser beam splitter 1504, an AC/RF signal generator 1508, amplifiers 1510 (e.g., in an embodiment, high voltage amplifiers), phase shifters 1512, a photoconductive antenna array 1506, and a terahertz beam combiner 1514. In an embodiment, laser 1502 is coupled to laser beam splitter 1504, which is in turn coupled to a photoconductive antenna array 1506. In an embodiment, photoconductive antenna array 1506 is adjusted by phase shifters 1512. In an embodiment, phase shifters 1512 receive a signal from AC/RF signal generator 1508 that has been amplified by high voltage amplifiers 1510. In an embodiment, the outputs of photoconductive antenna array 1506 are combined by terahertz beam combiner 1514 to produce a combined terahertz beam 1516.

In FIG. 15, the phase of terahertz beam 1516 is controlled by the distance between laser beam splitter 1504 and each terahertz photoconductive antenna in photoconductive antenna array 1506, the distance between each terahertz photoconductive antenna and terahertz beam combiner 1514, and by phase shifters 1512 for the AC/RF bias voltage, which is fed to photoconductive antenna array 1506 for terahertz beam amplification. In an embodiment, each photoconductive antenna can take as much as 120 mW femtosecond laser beam and can produce more than 3 mW average terahertz power, and the terahertz beam is predominantly coherent. So one can achieve a higher terahertz power by adding more photoconductive antennas to photoconductive antenna array 1506, as long as each split femtosecond laser beam has enough power to drive the photoconductive antenna to produce a terahertz beam. With a proper phase control, combined terahertz beam 1516 should maintain the same frequency spectrum of a terahertz beam that is produced by a single terahertz photoconductive antenna. In fact, this has been demonstrated through our experiments.

Figure 16:
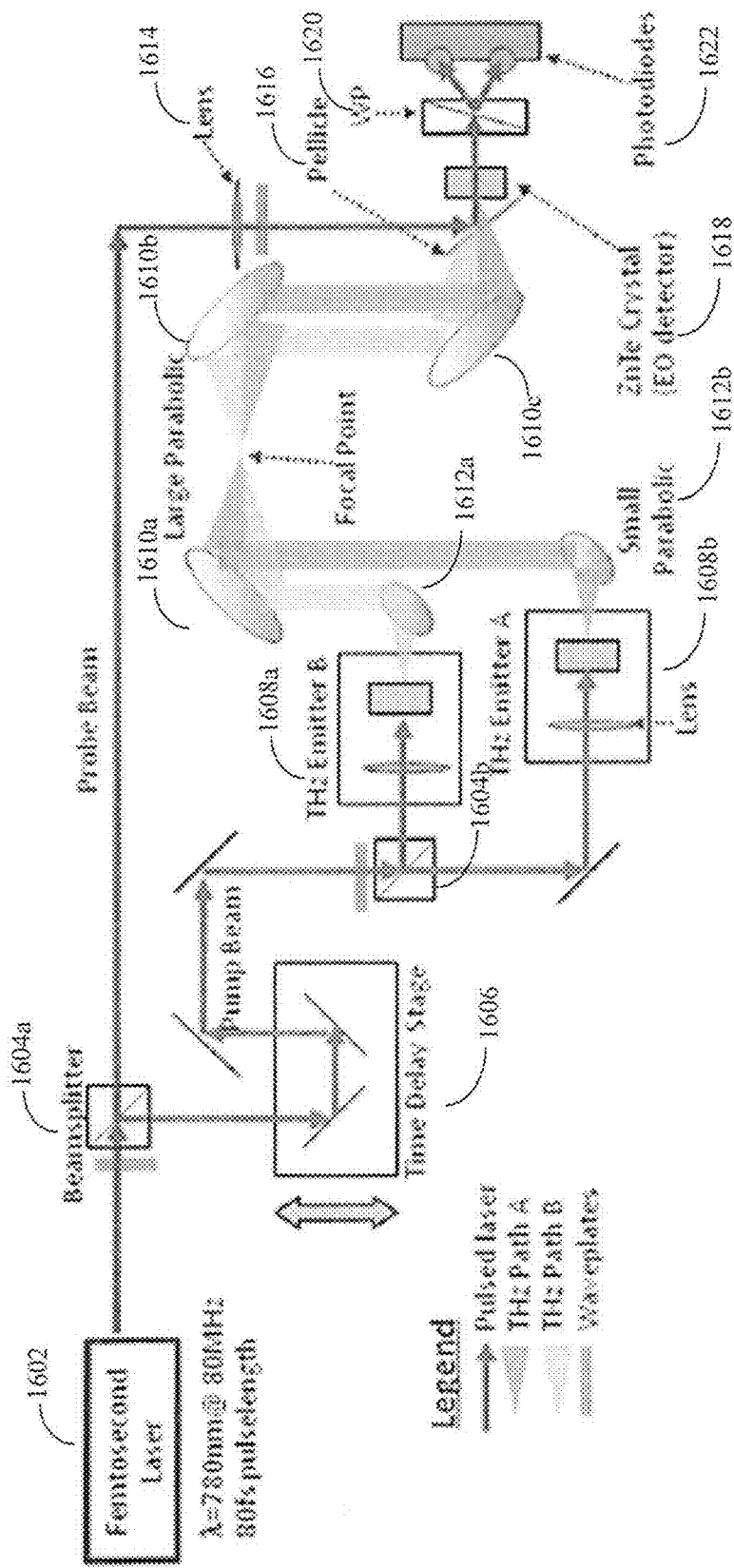
FIG. 16 is a schematic diagram of a time domain terahertz spectrometer (TDTS) using two arrayed terahertz photoconductive antennas in accordance with an embodiment of the present disclosure.

FIG. 16 is a schematic diagram of a time domain terahertz spectrometer (TDTS) using two arrayed terahertz photoconductive antennas in accordance with an embodiment of the present disclosure. In an embodiment, the TDTS of FIG. 16 includes a laser 1602 (e.g., in an embodiment, a femtosecond laser), a plurality of beamsplitters 1604, a time delay stage 1606, a plurality of THz emitters 1608, a plurality of large parabolic mirrors 1610, a plurality of small parabolic mirrors 1612, a lens 1614, a pellicle 1616, a crystal 1618 (e.g., a ZnTe crystal that acts as an EO detector), a waveplate 1620, and photodiodes 1622.

In an embodiment, laser 1602 is split by beamsplitter 1604a. Part of the split beam is delayed by time delay stage 1606 and is split again by beamsplitter 1604b. The split beams are sent to respective THz emitters 1608, which pass the respective beams, via respective parabolic mirrors 1610 and 1612, to crystal 1618. Crystal 1618 also receives another part of the beam split by beamsplitter 1604a. The beams are passed through crystal 1618, through WP 1620, to photodiodes 1622.

Experimental results generated by the TDTS spectrometer of FIG. 16 demonstrate that arrayed terahertz antennas described above with reference to FIG. 15 can produce a higher terahertz beam power and that the arrayed emitter can maintain the same frequency spectrum. For example, experimental results generated based on the TDTS of FIG. 16 indicate that a terahertz signal from a photoconductive antenna and another terahertz signal from another photoconductive antenna can be constructively added to produce a stronger terahertz signal.

In an embodiment, parabolic mirrors (e.g., parabolic mirrors 1610 and 1612) are used for combining terahertz beams. However, it should be understood that other beam combining techniques can be used to combine terahertz beams in accordance with embodiments of the present disclosure.

The high power terahertz photoconductive antenna array provided by embodiments of the present disclosure has several advantages. For example, the terahertz emitter based on terahertz photoconductive antenna arrays is small in size. An entire arrayed emitter system can be as small as 2×3×0.5 ft3, assuming that the system consists of 100 photoconductive antennas, a femto-second laser, beam splitters, beam combiners, AC signal generator, AC signal amplifier, and phase shifters. Further, the emitter is scalable. Terahertz power can be increased by adding more photoconductive antenna arrays. An emitter with 100 photoconductive antenna arrays can produce a terahertz beam more than 300 mW of average power and 37.5 kW of peak power. To date, no other portable source can produce such a high power terahertz beam. This emitter produces a broadband terahertz signal, of which frequency bandwidth can cover from 50 GHz to 3.5 THz. This frequency bandwidth can be adjusted by modifying the photoconductive antenna. Terahertz power strength can be easily controlled by adjusting the AC bias voltage signal. Additionally, one can modulate the terahertz signal either in the amplitude modulation (AM) mode or the frequency modulation (FM) mode.

3. Concluion

It is to be appreciated that the Detailed Description, and not the Abstract, is intended to be used to interpret the claims. The Abstract may set forth one or more but not all exemplary embodiments of the present disclosure as contemplated by the inventor(s), and thus, is not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Any representative signal processing functions described herein can be implemented using computer processors, computer logic, application specific integrated circuits (ASIC), digital signal processors, etc., as will be understood by those skilled in the art based on the discussion given herein. Accordingly, any processor that performs the signal processing functions described herein is within the scope and spirit of the present disclosure.

The above systems and methods may be implemented as a computer program executing on a machine, as a computer program product, or as a tangible and/or non-transitory computer-readable medium having stored instructions. For example, the functions described herein could be embodied by computer program instructions that are executed by a computer processor or any one of the hardware devices listed above. The computer program instructions cause the processor to perform the signal processing functions described herein. The computer program instructions (e.g., software) can be stored in a tangible non-transitory computer usable medium, computer program medium, or any storage medium that can be accessed by a computer or processor. Such media include a memory device such as a RAM or ROM, or other type of computer storage medium such as a computer disk or CD ROM. Accordingly, any tangible non-transitory computer storage medium having computer program code that cause a processor to perform the signal processing functions described herein are within the scope and spirit of the present disclosure.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments.

What is claimed is:

1. A photoconductive antenna array device, comprising:
   a beam splitter configured to receive a laser beam and to output a plurality of split laser beams;
   a plurality of antennas configured to receive respective split laser beams from the beam splitter;
   a plurality of phase shifters, coupled to respective antennas in the plurality of antennas, configured to adjust the respective antennas; and
   a beam combiner, coupled to respective outputs of the plurality of antennas, configured to generate a combined beam, wherein a phase of the combined beam is determined by a distance between a first antenna in the plurality of antennas and the beam combiner.

2. The photoconductive antenna array device of claim 1, wherein a phase of the combined beam is determined by respective distances between each respective antenna in the plurality of antennas and the beam combiner.

3. The photoconductive antenna array device of claim 1, wherein a phase of the combined beam is determined by adjustment of the plurality of phase shifters.

4. The photoconductive antenna array device of claim 1, wherein a phase of the combined beam is determined by a distance between the beam splitter and a first antenna in the plurality of antennas.

5. The photoconductive antenna array device of claim 1, wherein a phase of the combined beam is determined by respective distances between the beam splitter and each respective antenna in the plurality of antennas.

6. The photoconductive antenna array device of claim 1, wherein a first antenna in the plurality of antennas comprises:
   a substrate comprising a pair of trenches;
   a pair of non-parallel electrodes each deposited in one of the trenches, and configured to produce chaotic trajectories of incoherent electric currents; and
   an insulation layer between each of the pair of non-parallel electrodes and the trench walls.

7. The photoconductive antenna array device of claim 6, wherein a thickness of the substrate, a thickness of the trenches, and a thickness of the non-parallel electrodes are each optimized to produce a coherent terahertz beam.

8. The photoconductive antenna array device of claim 6, wherein the pair of non-parallel electrodes each comprise a chaotic electrode geometry.

9. The photoconductive antenna array device of claim 8, wherein the chaotic electrode geometries comprise one of:
   a circle plus arc electrode geometry;
   a ripple electrode geometry;
   a stadium concave geometry; or
   an hourglass geometry.

10. The photoconductive antenna array device of claim 6, wherein the insulation layer comprises at least one of a physical electrical insulation layer or an air gap.

11. A photoconductive antenna array device, comprising:
    a beam splitter configured to receive a laser beam and to output a plurality of split laser beams;
    a plurality of antennas configured to receive respective split laser beams from the beam splitter;
    a plurality of phase shifters, coupled to respective antennas in the plurality of antennas, configured to adjust the respective antennas; and
    a beam combiner, coupled to respective outputs of the plurality of antennas, configured to generate a combined beam, wherein a phase of the combined beam is determined by respective distances between the beam splitter and each respective antenna in the plurality of antennas.

12. The photoconductive antenna array device of claim 11, wherein the phase of the combined beam is further determined by respective distances between each respective antenna in the plurality of antennas and the beam combiner.

13. The photoconductive antenna array device of claim 11, wherein a phase of the combined beam is further determined by adjustment of the plurality of phase shifters.

14. A photoconductive antenna array device, comprising:
a laser configured to generate a laser beam;
a beam splitter configured to receive the laser beam and to output a plurality of split laser beams;
a plurality of antennas configured to receive respective split laser beams from the beam splitter;
a plurality of phase shifters, coupled to respective antennas in the plurality of antennas, configured to adjust the respective antennas; and
a beam combiner, coupled to respective outputs of the plurality of antennas, configured to generate a combined beam, wherein a phase of the combined beam is determined by:
first respective distances between the beam splitter and each antenna in the plurality of antennas,
second respective distances between each respective antenna in the plurality of antennas and the beam combiner, and
respective bias voltages of the plurality phase shifters.

15. The photoconductive antenna array device of claim 14, wherein the laser is a femtosecond laser.

16. The photoconductive antenna array device of claim 14, further comprising:
a plurality of amplifiers, wherein the plurality of amplifiers are coupled to respective phase shifters in the plurality of phase shifters.

17. The photoconductive antenna array device of claim 14, wherein the plurality of antennas form a photoconductive antenna array.

18. The photoconductive antenna array device of claim 14, wherein the beam combiner is a terahertz beam combiner that is configured to generate a terahertz beam, wherein the plurality of antennas are terahertz photoconductive antennas, and wherein each antenna in the plurality of antennas is configured to produce more than 3 mW average terahertz power.

19. The photoconductive antenna array device of claim 14, further comprising:
a ZnTe crystal configured to act as a detector.

20. The photoconductive antenna array device of claim 14, further comprising:
a time delay stage configured to delay a split laser beam in the plurality of split laser beams.

* * * * *